(12) United States Patent
Minakuchi et al.

(10) Patent No.: US 8,634,611 B2
(45) Date of Patent: Jan. 21, 2014

(54) REPORT GENERATION SUPPORT APPARATUS, REPORT GENERATION SUPPORT SYSTEM, AND MEDICAL IMAGE REFERRING APPARATUS

(75) Inventors: Maki Minakuchi, Otawara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1135 days.

(21) Appl. No.: 12/536,007

(22) Filed: Aug. 5, 2009

(65) Prior Publication Data
US 2010/0034442 A1 Feb. 11, 2010

(30) Foreign Application Priority Data
Aug. 6, 2008 (JP) ................................. 2008-202582

(51) Int. Cl.
*G06K 9/00* (2006.01)

(52) U.S. Cl.
USPC ............................ 382/128; 382/159; 382/305

(58) Field of Classification Search
None
See application file for complete search history.

(56) References Cited

U.S. PATENT DOCUMENTS

| 5,367,631 | A * | 11/1994 | Levy ............................... 345/163 |
| 5,991,729 | A * | 11/1999 | Barry et al. ........................ 705/3 |
| 6,272,470 | B1 * | 8/2001 | Teshima ............................ 705/3 |
| 7,873,526 | B2 * | 1/2011 | Iwasa et al. ........................ 705/2 |
| 7,899,684 | B2 * | 3/2011 | Fukatsu et al. ..................... 705/2 |
| 8,189,888 | B2 * | 5/2012 | Takahashi ....................... 382/128 |
| 2003/0177446 | A1 * | 9/2003 | Gropper et al. ................. 715/522 |
| 2004/0081342 | A1 * | 4/2004 | Sato ............................... 382/128 |
| 2004/0107118 | A1 * | 6/2004 | Harnsberger et al. .............. 705/2 |
| 2005/0226405 | A1 | 10/2005 | Fukatsu et al. |
| 2006/0271403 | A1 * | 11/2006 | Iwasa et al. ........................ 705/2 |
| 2007/0016453 | A1 * | 1/2007 | Hiyama et al. ..................... 705/3 |
| 2007/0150562 | A1 * | 6/2007 | Stull et al. ...................... 709/223 |
| 2007/0237376 | A1 * | 10/2007 | Yoshida ......................... 382/128 |
| 2008/0052112 | A1 * | 2/2008 | Zahlmann et al. ................. 705/2 |
| 2008/0086335 | A1 | 4/2008 | Matsue et al. |
| 2011/0004595 | A1 * | 1/2011 | Yamagishi et al. ........... 707/739 |

FOREIGN PATENT DOCUMENTS

| JP | 11-232364 A | 8/1999 |
| JP | 2001-118015 A | 4/2001 |
| JP | 2004-305289 A | 11/2004 |
| JP | 2005-301453 | 10/2005 |

OTHER PUBLICATIONS

Japanese Office Action issued Jul. 2, 2013 in Patent Application No. 2009-170807 with English-language Translation.

* cited by examiner

*Primary Examiner* — Nancy Bitar
(74) *Attorney, Agent, or Firm* — Oblon, Spivak, McClelland, Maier & Neustadt, L.L.P.

(57) ABSTRACT

A first display displays a medical image based on medical image data. A second display displays a generation screen for generating a string of a medical imaging report. A display controller causes the first display and the second display to display images. An operation part is for operating a pointer displayed on the first display and the second display. An annotation generator receives designation of a position on the medical image displayed on the first display by using the pointer, and attaches sign data representing a position specification sign to the medical image data. An address information acquiring part acquires address information for reading out the medical image data to which the sign data is attached. A linking part links the address information to a link object such as a string designated by using the pointer and displayed on the generation screen displayed on the second display.

13 Claims, 6 Drawing Sheets

REPORT GENERATION SUPPORT APPARATUS, REPORT GENERATION SUPPORT SYSTEM, AND MEDICAL IMAGE REFERRING APPARATUS

BACKGROUND OF THE INVENTION

1. Field of the Invention

The present invention relates to a report generation support apparatus that generates a medical imaging report for reporting the result of interpretation of a medical image, a report generation support system, and a medical image referring apparatus. More specifically, the present invention relates to a report generation support technique of generating a link of a medical image corresponding to a link destination such as a string in a comment field of a medical imaging report.

2. Description of the Related Art

Since medical practice is segmentalized into specialized fields, interpretation of a medical image captured by a conventional image diagnosis apparatus is generally asked to a radiologist. A radiologist displays a medical image that the radiologist is asked to interpret on a monitor, and writes a medical imaging report on the interpretation result.

Moreover, at the time of interpretation, a radiologist displays a medical image for comparison with an interpretation object, or displays a previous medical imaging report of the patient or a medical imaging report on the result of interpretation of a comparison medical image, and uses them as reference materials.

In recent years, it has become common to display a report generation screen on a monitor to electronically generate a medical imaging report. In a report generation support apparatus, an operator inputs a comment about a medical image to be interpreted into a comment field.

Then, regarding an image indicated in the comment, the operator specifies a link corresponding range with respect to a string already inputted into the comment field, and executes linking to the string therein. Alternatively, there is a case that a report to be a link destination other than the string is designated and the image is directly linked to the corresponding report.

Furthermore, in linking of a medical image to a link object such as a string, the operator designates a medical image to be linked, drags from the medical image, and drops the medical image onto a link object of a link destination. By this drag-and-drop operation, address information indicating a storing place of the designated medical image is linked to the link object on which the medical image has been dropped.

In a case that the link destination is a string, by changing the color of the link destination string and underlining it simultaneously with the linking, the string is identified. Such a linking technique by the drag-and-drop operation is proposed (e.g., Japanese Unexamined Patent Publication No. 2005-301453).

Owing to the medical imaging report generation technique by linking, the efficiency in interpretation has increased.

However, in a case that a link is merely put to an image as in JP-A 2005-301453, it is difficult to grasp what part in a medical image is indicated by the content of a comment field at a glance. Accordingly, in order to make it possible to grasp what part in a medical image is indicated by the content of a comment field, the operator needs to manually attach, to the medical image, an annotation such as an arrow that indicates the part in the medical image indicated by the content of the comment field.

Further, comments written in the comment field may indicate various different parts in one sheet of medical image. In this case, it is difficult, by merely attaching a plurality of annotations to the medical image, to grasp the correspondence relation between the comments in the comment field and the annotations. Accordingly, the operator needs to display the correspondence relation by, e.g., manually attaching the same signs to a comment in the comment field and to an annotation in the medical image corresponding to the content. Such a method of manually generating annotations and generating signs that represent the correspondence relation lowers the operation efficiency because much time is spent for generation of the annotations and signs.

SUMMARY OF THE INVENTION

The present invention was made in view of such circumstances, and an object of the present invention is to provide a report generation support technique for automatically generating an annotation at a part of a medical image indicated in a comment field.

Further, another object of the present invention is to provide a report generation support technique of automatically generating a sign that represents a correspondence relation between each annotation and a link destination such as a string corresponding to the annotation described in a commend field of a medical imaging report.

A report generation support apparatus in a first aspect of the present invention is provided with function parts described below. A first display displays a medical image based on medical image data. A second display displays a generation screen for generating a string of a medical imaging report. A display controller causes the first display and the second display to display an image. An operation part is for operating a pointer displayed on the first display and the second display.

An annotation generator receives designation of a position on the medical image displayed on the first display by using the pointer, and attaches sign data representing a position specifying sign to the medical image data. An address information acquiring part acquires address information for reading out the medical image data to which the sign data is attached. A linking part links the address information to link destination such as the string designated by using the pointer on the generation screen displayed on the second display.

A report generation support system in a second aspect of the present invention is provided with a medical image diagnosis apparatus configured to generate a medical image; a medical image referring apparatus configured to display a medical image generated by the medical image diagnosis apparatus; a report generating apparatus configured to display a generation screen of a medical imaging report based on the medical image displayed by the medical image referring apparatus; and an operation part for operating a pointer displayed on a display of the medical image referring apparatus and a display of the report generating apparatus. The medical image referring apparatus is provided with function parts described below. A position specifying part receives designation of a position on the medical image by using the pointer, and specifies medical image data of a part corresponding to the medical image at the position. An annotation generator attaches sign data for representing a position specifying sign that makes it possible to view the position on the medical image based on the medical image data of the specified part, to the medical image data. Moreover, the report generating apparatus is provided with function parts described below.

An address acquiring part acquires a storing destination address of the medical image data to which the sign data is attached. A linking part, when a link destination such as a string displayed on the generation screen is designated by using the pointer, links the storing destination address to the link destination.

A medical image referring apparatus in a third aspect of the present invention is provided with function parts described below. An operation part is for operating a pointer displayed on the display. A position specifying part receives designation of a position on the medical image by using the pointer, and specifies medical image data of a part corresponding to the medical image at the position. An annotation generator attaches sign data for representing a position specifying sign that makes it possible to view the position on the medical image based on medical image data of the specified part, to the medical image data.

A report generation support apparatus in a fourth aspect of the present invention is provided with function parts described below. A first display displays a medical image based on medical image data. A second display displays a generation screen for generating a medical imaging report. An operation part is used for operating a pointer displayed on the first display and the second display. An annotation generator, in response to operation input of the pointer for linking the medical image data of the medical image displayed on the first display to the medical imaging report, attaches, to the medical image data, sign data representing a position designated by the operation input on the medical image displayed on the first display. A linking part links the medical imaging report to the medical image data for the operation input.

The report generation support apparatus in the first aspect, the report generation support system in the second aspect, the medical image referring apparatus in the third aspect, and the report generation support apparatus in the fourth aspect are each configured to, when linking a referred medical image and a link destination such as a string in a comment generated with reference to the medical image, automatically attach a position specifying sign to a position designated on a medical image. This enables the operator to eliminate the operation of attaching a position specifying sign to a position on a medical image corresponding to a link destination such as a string written in a comment field of a medical imaging report, and to facilitate the operation for easily grasping the position on the medical image indicated by the content of the link destination such as the string of the comment field.

DETAILED DESCRIPTION OF THE EMBODIMENTS

First Embodiment

A report generation support apparatus according to a first embodiment of the present invention will be described below.

Figure 1:
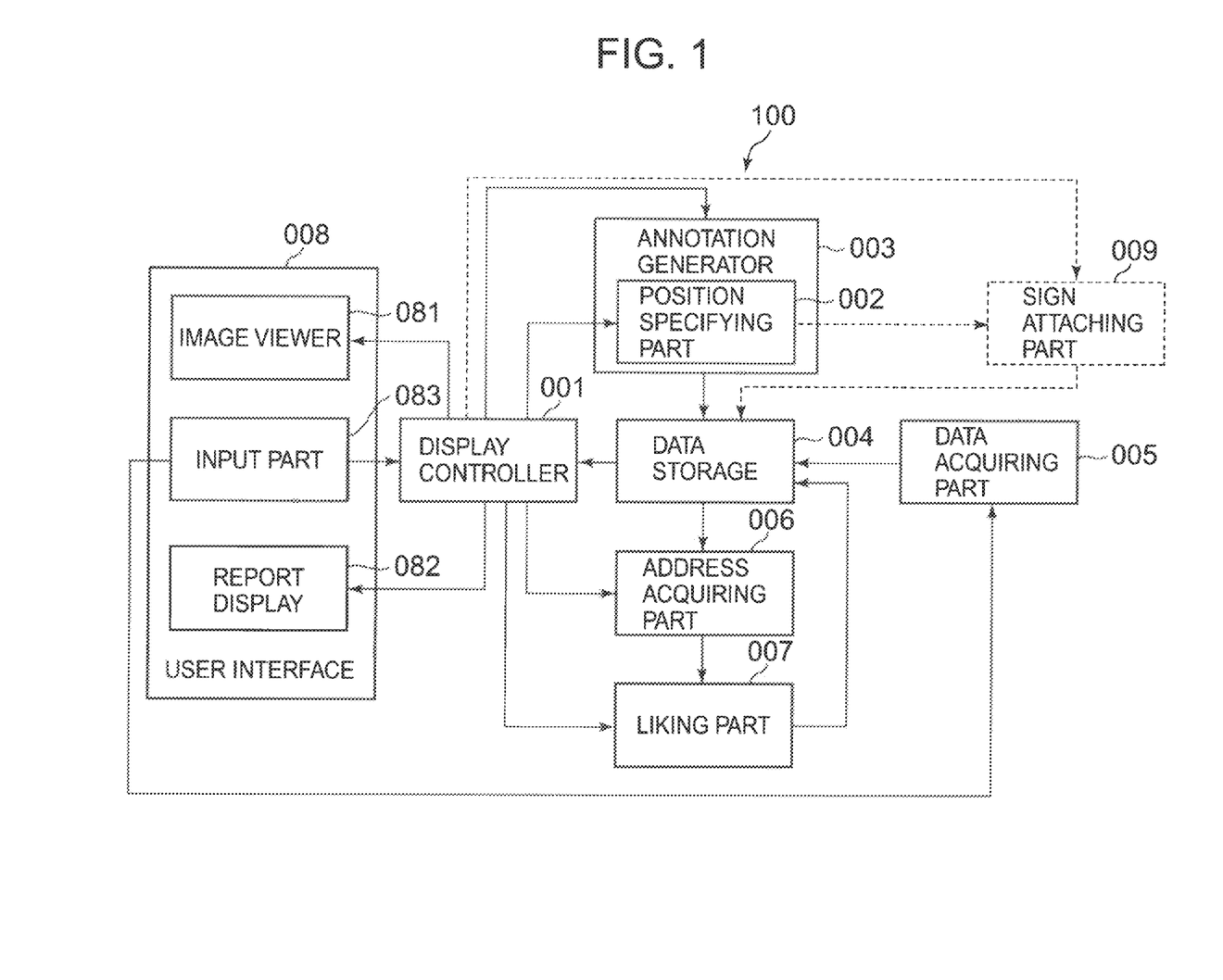
FIG. 1 is a block diagram of a report generation support apparatus according to the present invention.
Figure 2:
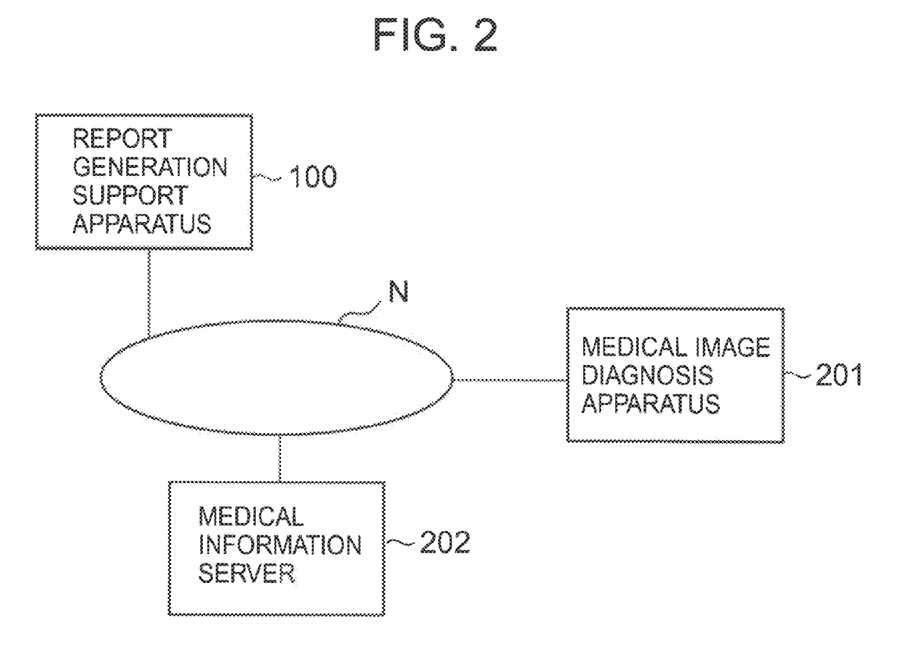
FIG. 2 is a schematic configuration diagram showing a system configuration of a report generation support system according to the present invention.

FIG. 1 is a block diagram showing the function at the time of generation of a medical imaging report in a report generation support apparatus according to the present invention. FIG. 2 is a schematic configuration diagram showing a system configuration of a report generation support system according to the present invention. A medical imaging report may be simply referred to as a "report" hereinafter.

Further, although a string is used as a link destination in the description below, the link destination may be any other thing. For example, a whole report may be the link destination. This is true to other embodiments.

(System Configuration)

The report generation support apparatus according to the present embodiment is configured as part of a hospital information system. In this hospital information system, as shown in FIG. 2, a plurality of medical diagnosis apparatuses 201 including an X-ray CT apparatus, an MRI apparatus and an ultrasound diagnosis apparatus, a report generation support system 100 according to the present invention, and a medical information server 202 are connected via a network N so as to be capable of mutually transmitting and receiving information.

The medical information server 202 stores medical information generated in a hospital so that medical information including medical images and medical imaging reports are shared. The medical information server 202 includes a hospital information system server, a medical image server and a report server, which are not shown in the drawings.

In response to a search request or a transmission request by a computer terminal connected to the network N, the medical information server 202 searches the stored medical information and transmits relevant medical information to the computer terminal.

The report generation support apparatus 100 is installed in, for example, a radiology reading room, and generates an electronic file of reports on medical images required to be interpreted. The report generation support apparatus 100 receives a medical image required to be interpreted or a previous medical imaging report that a medical image to be interpreted from the medical information server 202, and displays it.

The report generation support apparatus 100 also displays a report generation screen, and an operator (simply referred to as an "operator" hereinafter) inputs a string into a comment or links a medical image to the string in accordance with the operation of the operator.

The network N is an electronic communication line capable of transfer of electronic data. The report generation support apparatus 100 and the medical information server 202 communicate electronic data by a network communication technique such as DICOM (Digital Imaging and Communication Medicine) protocol via the network N.

(Generation of Link)

An operation by the operator for the report generation support apparatus according to the present embodiment will be described. When generating a link of a referred medical image to a string in a comment, the operator designates, by using a pointer, a position on the medical image corresponding to the content of the string, on the referred medical image. Then, the operator drags (moves) the pointer from the designated position and drops it on the corresponding string. Through this operation, the operator designates a link destination string. This operation will be referred to as a drag-and-drop operation hereinafter.

In the description hereinafter, a position on a medical image designated by using the pointer as a position corresponding to the content of a string on the medical image is referred to as a position of a drag origin, and the point of the position is referred to as a point of the drag origin. The pointer is a marker that indicates a position on a screen.

The designation of a position on a medical image and the designation of a link object on a report (e.g., an operation from the designation of the position on the medical image to the designation of a string of the link object by drag-and-drop in the above description) are equivalent to the "operation input" of "linking the medical image data of the medical image to the medical imaging report" in the present invention.

The report generation support apparatus 100 is a workstation connected to the network N. A workstation is a so-called computer that has hardware such as a CPU, a memory and a hard disk.

The report generation support apparatus 100 has two displays of an image viewer 081 and a report display 082, and an input part 083, as a user interface 008 as shown in FIG. 1. The image viewer 081 is equivalent to a "first display" of the present invention. Moreover, the report display 082 is equivalent to a "second display" of the present invention. A medical image, a medical imaging report, etc. are displayed on the image viewer 081 and the report display 082 by output of drawing data by the display controller 001. The input part 083 is composed of a keyboard, a mouse, etc.

Both input to a screen displayed on the image viewer 081 and input to a screen displayed on the report display 082 are conducted through the input part 083. Since the image viewer 081 and the report display 082 are placed side by side physically, it is possible to seamlessly move a pointer displayed on the screen between the image viewer 081 and the report display 082 by moving the mouse, which is one of the input part 083.

The operator inputs identification information, such as patient ID and examination UID of a medical image to be interpreted and a previous medical imaging report to be referred, to a data acquiring part 005 by using the input part 083.

The data acquiring part 005 receives identification information of a medical image and of a medical imaging report, and acquires medical data such as the medical image and the medical imaging report from a medical information server 202. The data acquiring part 005 then outputs the acquired medical data to a data storage 004.

The data storage 004 is composed of a storing medium such as a memory and a hard disk. The data storage 004 stores the medical data inputted from the data acquiring part 005.

The display controller 001 causes the image viewer 081 to display a medical image to be interpreted or previous medical imaging report stored in the data storage 004. Moreover, the display controller 001 causes the report display 082 to display a report generation screen.

This report generation screen is displayed in a format previously stored by the display controller 001. Furthermore, when characters and the like are inputted to the displayed report generation screen, the display controller 001 causes the report generation screen of the report display 082 to display the characters in response to the input.

Figure 3:
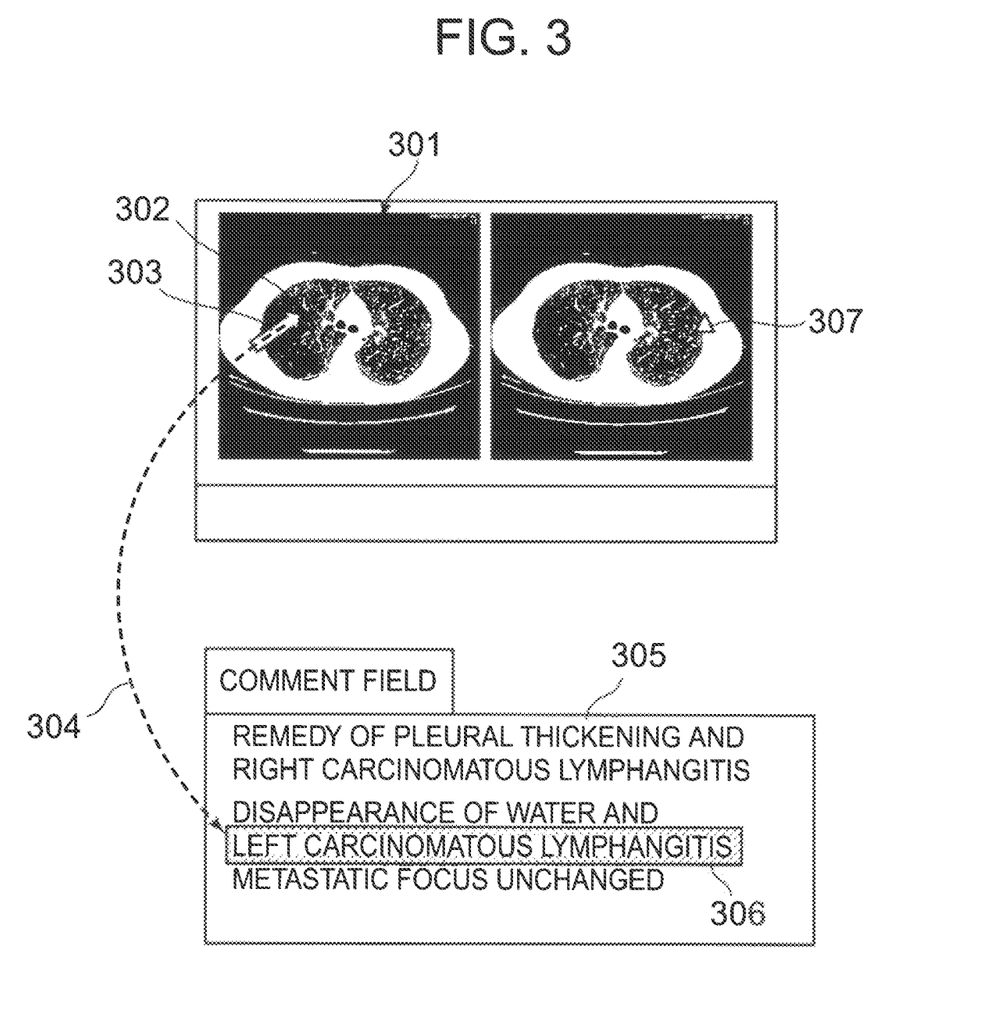
FIG. 3 is a view for describing an operation of generating a link.

An operation by the operator for generating a link of the address of a medical image referred for generation of a comment, to a specific string in a comment field at the time of generation of a medical imaging report will be described with reference to FIG. 3. FIG. 3 is a view for describing an operation of generating a link.

Before executing the drag-and drop operation (a dashed-line arrow 304), the operator selects an annotation attached to a medical image in the drag-and-drop operation, from among plural kinds of annotations displayed so as to be selectable on the report display 082.

The plural kinds of annotations are stored in a storage (not shown) of the report generation support apparatus. Then, the display controller 001 reads out the annotations stored in the storage and causes the report display 082 to display them. The annotation is a sign such as an arrow indicating a specific portion in an image. The annotation is equivalent to a "position specifying sign" in the present invention. In this embodiment, it is possible to select an arrow or a template previously made by the operator (e.g., a template of attaching a plurality of arrows) as the annotation. A case that the operator selects an arrow as the annotation will be described below.

The operator selects a string 306 written in a comment field 305 of the report generation screen by using the mouse of the input part 083.

Then, the operator moves a pointer to a point 302 of a medical image 301 indicated by the content shown by the string 306 and designates the position by using the mouse of the input part 083. This designated position becomes a drag origin. The operator then drags the pointer from the drag origin to the selected string 306 in the commented field 305, and drops the pointer at the position of the string 306. The drop is equivalent to "designation of a string" in the present invention.

Movement in the drag-and-drop operation is represented by the dashed-line arrow 304.

The display controller 001 receives input of designation of the position of the drag origin from the input part 083, and outputs the coordinates on the image viewer 081 of the position of the medical image 301 and the coordinates on the image viewer 081 of the point 302 of the drag origin of the pointer, to a position specifying part 002. The coordinates of the position of the medical image 301 mean the position of each side or each vertex of the medical image 301.

Further, the display controller 001 receives input of drag from the input part 083, and outputs the identification information of the medical image 301 displayed at the drag origin, to the annotation generator 003 and an address acquiring part 006.

Furthermore, the display controller 001 receives input of drop from the input part 083, and outputs the identification information of the string 306 on which the pointer has been dropped, to a linking part 007. The identification information of the string 306 on which the pointer has been dropped is information, for example, what comment includes the string 306 and from what number to what number of characters compose the string 306. Moreover, determination of what comment is made by determining what number from above the comment is based on the number of linefeeds or, in a case that a comment number is put on the head of each comment, determining what comment based on the comment number.

The annotation generator 003 includes the position specifying part 002. Although the position specifying part 002 is configured as part of the annotation generator 003 in this embodiment, the annotation generator 003 and the position specifying part 002 may be configured as separate function parts.

The position specifying part 002 receives, from the display controller 001, the coordinates of the point 302 of the drag origin designated by the operator and the coordinates of the position of the displayed medical image 301, and specifies the drag origin point 302 on the medical image 301 displayed on the image viewer 081. Since the display controller 001 previously stores the coordinates of each point on the image viewer 081, the position specifying part 002 is capable of specifying the coordinates of the drag origin point 302, by acquiring the coordinates of the drag origin point 302 from the display controller 001.

Moreover, the position specifying part 002 can specify the position on the image viewer 081 of the medical image 301, by acquiring the positions of the respective sides or vertexes of the medical image 301, which are the coordinates of the position of the displayed medical image 301. Then, the position specifying part 002 obtains the position on the medical image 301 of the drag origin point 302, by obtaining the ratio from each of the vertexes of the medical image 301 to the drag origin point 302. To be specific, the position on the medical image 301 of the drag origin point 302 is represented, for example, a two-to-three position of a lateral side and a four-to-one position of a longitudinal side of the medical image 301. Specifying medical image data in the designated position on the medical image 301 is equivalent to "specifying medical image data of a designated portion of a medical image."

The position specifying part 002 outputs the position of the drag origin point 302 on the displayed medical image 301, to the annotation generator 003.

The annotation generator 003 receives input of the identification information of the displayed medical image 301, from the display controller 001. Furthermore, the annotation generator 003 receives input of the position of the drag origin point 302 on the displayed medical image 301, from the position specifying part 002.

The annotation generator 003 receives the type of the annotation inputted by the operator, and attaches the selected type of annotation 003 to the inputted position of the drag origin point 302 on the displayed medical image 301. Then, the annotation generator 003 stores information of the attached annotation 003 into the data storage 004. In this embodiment, attaching the annotation 303 is specifically, in association with the identification information of a medical image, storing the position and type (an arrow in this embodiment) of the annotation to be displayed when the medical image is displayed, into a database of the data storage 004. Thus, when displayed, the medical image 301 is displayed in a state that the designated type of annotation 303 is attached in the designated position. Besides, as a method for attaching an annotation, there are other methods such as storing as information of a medical image itself and storing annotation information into another file.

The address acquiring part 006 receives input of the identification information of the displayed medical image 301 from the display controller 001. Then, the address acquiring part 006 searches the database of the data storage 004 based on the inputted identification information, and extracts patient ID, examination UID, image UID and series UID from supplementary information of the medical image 301 having the inputted identification information, namely, the displayed medical image 301. Furthermore, the address acquiring part 006 generates a storing address URL of the medical image 301 written in HTML based on the extracted patient ID, examination UID, image UID and series UID.

The address acquiring part 006 outputs the generated URL to the linking part 007.

The linking part 007 receives input of the identification information of the string 306 on which the pointer has been dropped, from the display controller 001. Furthermore, the linking part 007 acquires the storing address URL of the displayed medical image 301, from the address acquiring part 006.

The linking part 007 links the medical image 301 to the string 306 on which the pointer has been dropped. The linking is associating the storing address URL of the medical image 301 with the string 306, and setting so as to cause the image viewer 081 to display the medical image 301 based on the associated storing address URL when a predetermined operation such as double-click is executed on the string 306 displayed on the report display 082. That is to say, the linking part 007 stores the storing address URL of the medical image 301 into the data storage 004 in association with the string so that the medical image 301 is displayed when the predetermined operation is executed on the string 306.

Furthermore, the linking part 007 stores identification information of the string 306 and identification information (e.g., position information on the medical image 301) of the annotation 303 corresponding to the string 306 generated by the annotation generator 003 in combination into the storage 004.

Furthermore, in response to the attachment of the annotation 303 onto the medical image 301 by the annotation generator 003, the display controller 001 may cause to temporarily display the annotation 303 attached on the displayed medical image 301. "Temporarily" may mean that the annotation 303 disappears on the medical image 301 after a given time, or that the annotation 303 disappears on the medical image 301 in response to input by the operator. Besides, imagery of a medical image to which the annotation is attached in the position designated on a medical image of a link object so as to follow near the moving pointer may be displayed during the linking operation (while a medical image is dragged and then dropped).

By thus temporarily displaying the attached annotation on the displayed medical image, the operator can determine whether the annotation is attached as the operator desires.

It is also possible to configure so that the operator can correct the attached annotation 303 by using the input part 083 when the annotation 303 is not attached as the operator desires. In this case, the operator designates the annotation 303 by using the mouse, and moves the designated annotation 303 by using the mouse. The position specifying part 002 specifies the position of the moved annotation 303. Then, the annotation generator 003 erases information of the annotation 303 attached and stored into the data storage 004 before the correction, attaches the annotation 303 to the position on the medical image 301 newly specified by the position specifying part 002, and stores the information into the data storage 004. By thus configuring, it becomes possible to correct the position of the attached annotation. Moreover, the operator designates the annotation 303 by using the mouse, displays a list of the annotation types by right-clicking the mouse, etc., and selects another type of annotation from the list. In response to this input, the annotation generator 003 changes the annotation 303 to the selected type of annotation, erases information of the attached annotation 303 stored into the data storage 004 before the change, and stores information of the changed type of annotation 303 into the data storage 004.

Furthermore, this temporary display may be conducted after the linking by the linking part 007 or before the linking by the linking part 007. In the case of temporarily displaying the attached annotation 003 before the linking by the linking part 007, the linking part 007 conducts the linking in response to input of determination of attachment of the annotation by the operator.

Further, it is possible to employ methods as described below as the method for correcting an attached annotation.
(1) At the time of dragging from an image to a link object in a report, an annotation is displayed as a preview (temporary display of an annotation). When the dragging state is released, a correctable mode is maintained for a predetermined time period, and the annotation can be corrected during the time period. After that, at the time of dragging again from the image to the link object in the report, a dragging mode is selected and the image is put to the link object in the report.

(2) At the time of dragging from an image to a link object in a report, an annotation is displayed as a preview. When the dragging state is released and a region in which the annotation to be corrected can be recognized is designated, it becomes possible to correct the annotation.

After that, a region other than the annotation to be corrected is designated, a dragging mode is selected, and the image is put to the link object in the report.

(3) In the case of attaching a plurality of annotations, at the time of dragging from an image to a link object in a report, an annotation is displayed as a preview. When the dragging state is released, a "correction completion button" is displayed. Then, the annotation is corrected by the method (1) or (2) described above. When the correction completion button is clicked after the correction and dragging is conducted from the image to the link object in the report, the image is put to the link object in the report. At this moment, until the "correction completion button" is pressed, the annotation is corrected after a lapse of a specified time, and it is possible to add an annotation by clicking on an image in the method (1). In the method (2), it is possible to add an annotation by clicking on an image other than a region in which the annotation to be corrected can be recognized. In the method of adding a plurality of annotation, a plural addition button may be provided.

As described above, by making it possible to correct an attached annotation, it becomes possible to more accurately attach an annotation as the operator desires.

(Reference of Medical Image)

When referring to a medical imaging report, the operator inputs identification information of the medical imaging report to be referred by using the input part 083. Moreover, when referring to a medical image with an annotation indicated by the content of a string having link information in a comment field of the medical imaging report displayed on the image viewer 081, the operator executes a predetermined operation such as double-click on the string and inputs an instruction to display the medical image linked to the string by using the input part 083.

The display controller 001 searches the data storage 004 based on the identification information inputted by using the user interface 008 and extracts a medical imaging report corresponding to the identification information. Then, the display controller 001 causes the image viewer 081 to display the extracted medical imaging report. At this moment, the display controller 001 attaches a sign (e.g., an underline) indicating "having link information" to a string with the link put from among strings written in the comment field, and causes to display the string.

The string having the link information can be specified by the display controller 001 referring to the position of the link stored in the data storage 004.

Further, upon reception of the input of the instruction to display the image linked to the string in the comment field of the medical imaging report displayed on the image viewer 081, the display controller 001 searches the data storage 004 based on an URL associated with the string and extracts the medical image linked to the string.

Furthermore, the display controller 001 refers to supplementary information of the extracted medical image to check whether there is an annotation and, in a case that there is an annotation, extracts the position and type of the annotation stored in the data storage 004. Then, the display controller 001 attaches the extracted type of annotation to the extracted position of the annotation together with the extracted medical image, and causes the image viewer 081 to display. An example of a medical image displayed with an annotation attached is the medical image shown in FIG. 3. In this embodiment, an arrow like the annotation 303 is displayed. Moreover, when the operator designates a triangle as an annotation, an annotation like an annotation 307 is displayed on the medical image.

Figure 4:
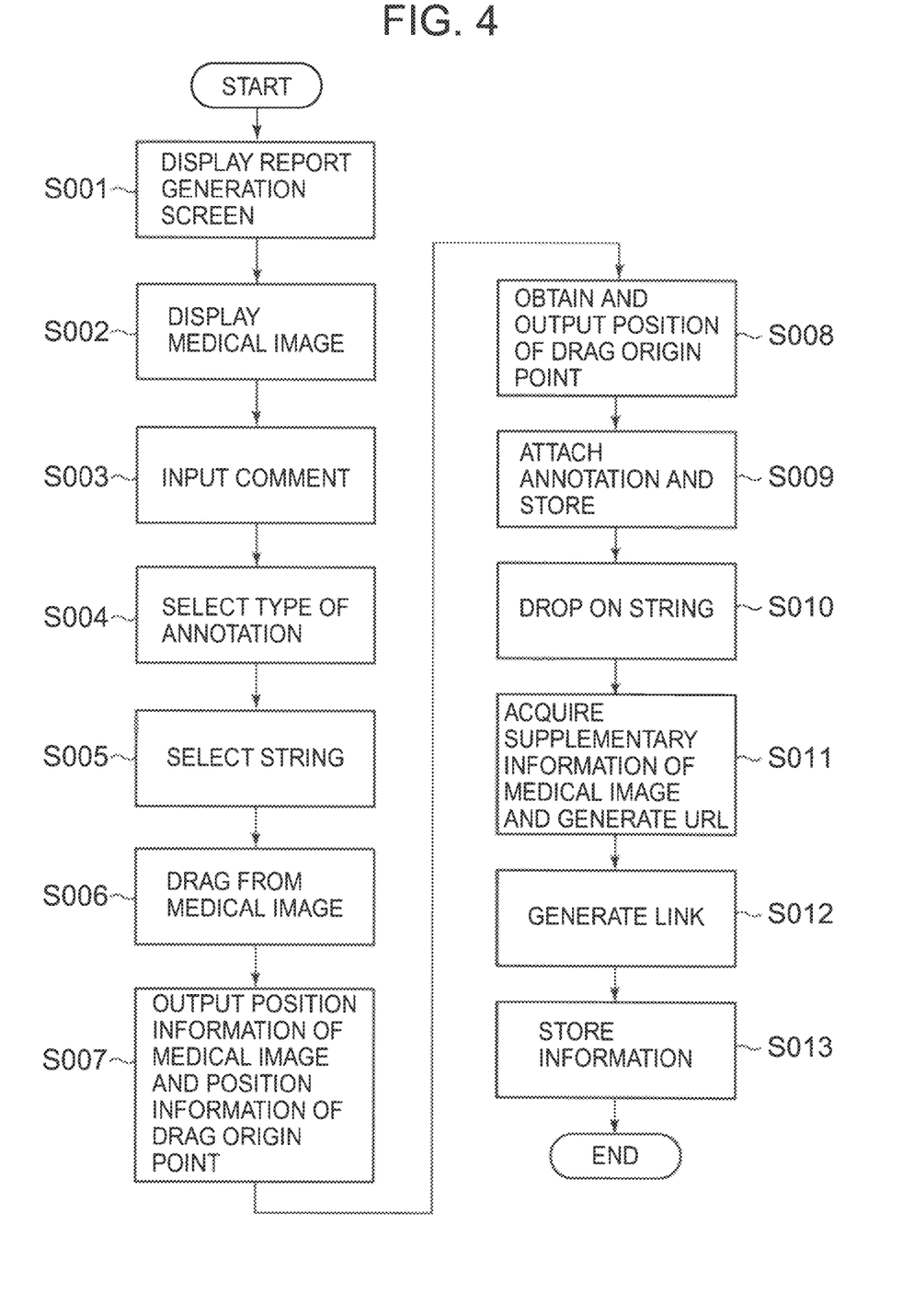
FIG. 4 is a flow chart of attachment of an annotation and generation of a link in a report generation support apparatus according to a first embodiment.

Next, with reference to FIG. 4, the flow of attachment of an annotation and generation of a link in the report generation support apparatus according to this embodiment will be described. FIG. 4 shows a flowchart of attachment of an annotation and generation of a link in the report generation support apparatus according to this embodiment.

Step S001: The display controller 001 receives a request for generation of a medical imaging report from the operator, and causes the report display 082 to display the report generation screen.

Step S002: The display controller 001 receives input of identification information of a reference image from the operator, and causes the image viewer 081 to display the reference medical image.

Step S003: The operator refers to the medical image displayed on the display viewer 081, and inputs a comment as a string into a comment field of the report generation screen displayed on the report display 082.

Step S004: The operator selects and inputs the type of an annotation desirable to attach by using the user interface 008.

Step S005: The operator selects a string to which it is desired to link in the comment field displayed on the report display 082.

Step S006: The operator places a pointer on a portion of the medical image corresponding to the content of the selected string, by using the user interface 008, and designates the position of a drag origin.

Step S007: The display controller 001 outputs position information of the medical image and position information of a drag origin point, to the position specifying part 002.

Step S008: The position specifying part 002 obtains position information of the drag origin point on the medical image, and outputs the position information of the drag origin point to the annotation generator 003.

Step S009: The annotation generator 003 attaches an annotation of the type inputted by the operator to the inputted position of the drag origin point, and stores into the data storage 004.

Step S010: The operator drags the pointer to the selected string by using the user interface 008, and drops on a place of the string.

Step S011: The address acquiring part 006 acquires identification information of the displayed medical image from the display controller 001, searches the data storage 004 based on the identification information, and acquires patient ID, examination UID and series UID written in supplementary information of the medical image. Furthermore, the address acquiring part 006 generates an URL of a storing address of the medical image based on the acquired information.

Step S012: The linking part 007, based on the identification information of the string with the pointer dropped inputted by the display controller 001 and the URL of the storing address of the medical image inputted by the address acquiring part 006, stores the string with the pointer dropped and the URL associated thereto into the data storage 004, and generates a link to the medical image onto the string.

Step S013: The data storage 004 receives a storing command by the operator, and stores the generated medical imaging report and the information attached to the medical imaging report such as the link and a key image.

Figure 5:
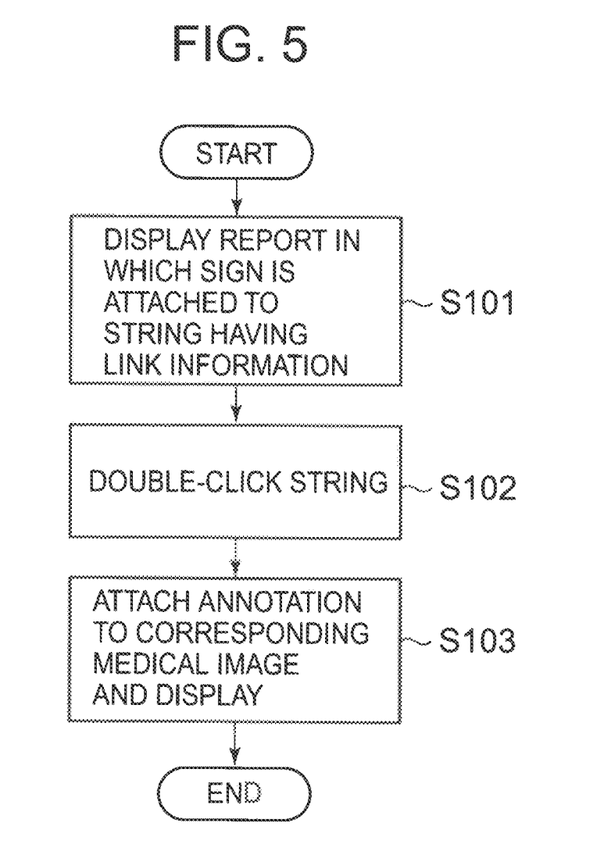
FIG. 5 is a flow chart of display of a linked medical image in the report generation support apparatus according to the first embodiment.

Next, with reference to FIG. 5, the flow in the case of selecting a string having link information in a comment field in the report generation support apparatus according to this embodiment will be described. FIG. 5 shows a flowchart of display of a linked medical image in the report generation support apparatus according to this embodiment.

Step S101: The display controller 001 receives an instruction to display a medical imaging report by the operator, acquires the designated medical imaging report and information of a string having link information in the medical imaging report, from the data storage 004, and causes the image viewer 081 to display the medical imaging report in which a sign is attached to the string having link information.

Step S102: The operator selects the string having the link information in the comment field, and executes double-click, etc., on the string.

Step S103: The display controller 001 searches the data storage 004 based on the URL of the storing address associated with the designated string, acquires a medical image associated with the string and the position and type of an annotation attached to the medical image, and causes the image viewer 081 to display the medical image and the annotation of the acquired type attached to the acquired position.

Although the linking operation by drag-and-drop is executed only one time in the above description, it may be executed plural times on the same string or different strings. In this case, an annotation is attached to each point of a drag origin at the time of dragging.

As described above, the report generation support apparatus according to the present invention is configured to, in order to put a link to a referred medical image onto a string in a comment field, automatically generate an annotation in a drag origin position on the medical image when executing drag-and-drop from the medical image to the string. Consequently, generation of an annotation onto a portion of a medical image corresponding to the content of a string, which has been executed by the operator, is executed automatically. Thus, it is possible to reduce the burden on the operator of generation of a medical imaging report, and it is also possible to increase the efficiency in operation.

Further, although drag-and-drop is executed from a medical image to a string of a medical imaging report in the above description, it may be executed with the string of the medical imaging report as a drag origin and with a place desired to designate on the medical image as a drop destination. In this case, information of a storing address of the drop destination medical image is sent to the address acquiring part 006, and linking is executed by the linking part 007. Then, the position specifying part 002 specifies the position designated by the pointer as the drop destination, and the annotation generator 003 attaches an annotation to the medical image based on the specified position.

Furthermore, although predetermined types of annotations are used in the above description, it is possible to configure so that the operator generates new types of annotations and uses these kinds of annotations. An example of this configuration will be described. The operator generates a new annotation by using the input part 083. Then, the report generation support apparatus receives input of the generated annotation, and adds the annotation to the storing part that stores plural kinds of annotations described above. When the operator displays a list the types of annotations for selection, the display controller 001 causes to display the list to which the newly generated annotation is attached.

By such a configuration, the operator can use an annotation generated by him/her.

Second Embodiment

Figure 6:
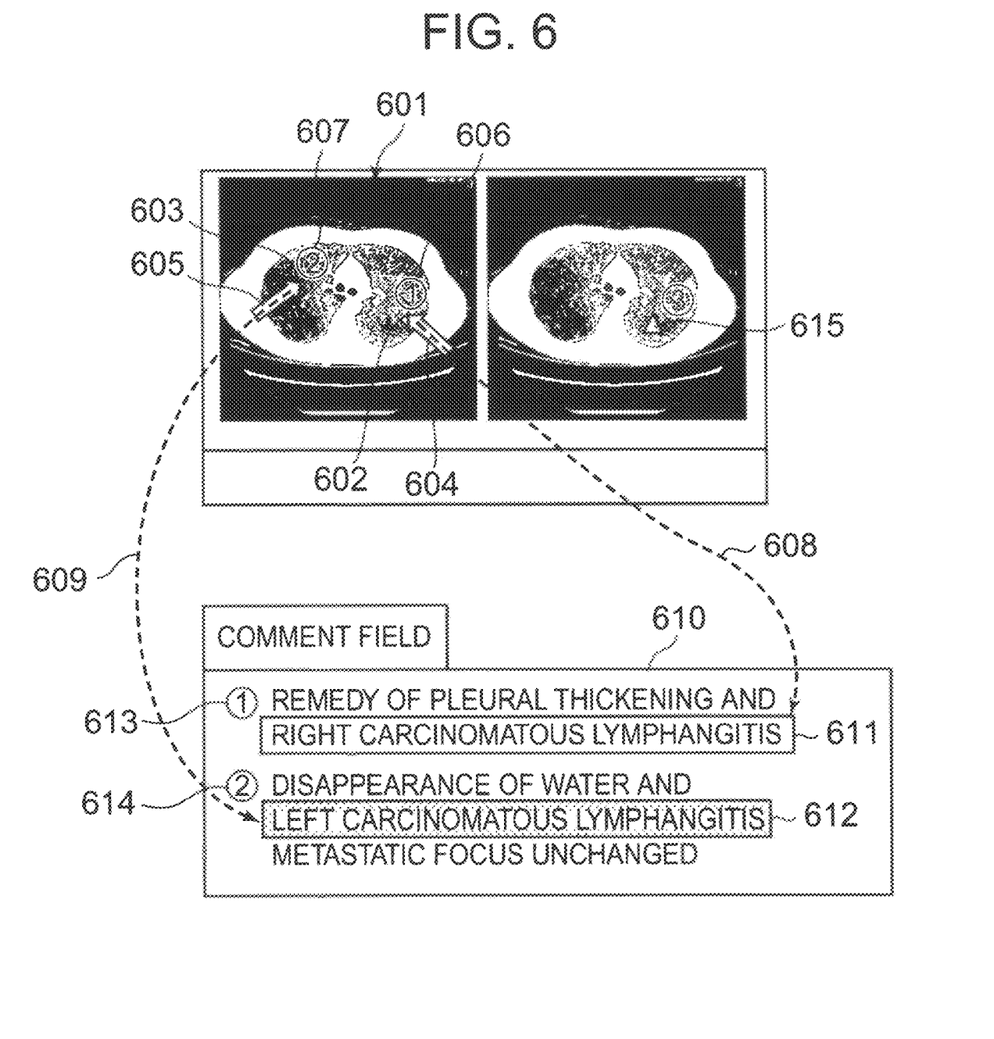
FIG. 6 is a view for describing an operation of generation of a link in a report generation support apparatus according to a second embodiment.

A report generation support apparatus according to a second embodiment of the present invention will be described below. The report generating apparatus according to this embodiment is different from the first embodiment in attaching a sign that represents a correspondence relation between a generated annotation and a string corresponding thereto. Therefore, a configuration and operation relating to attachment of a sign representing a correspondence relation will be mainly described. A block diagram showing the function of the report generation support apparatus according to this embodiment is shown by the function block of the first embodiment shown in FIG. 1 to which a function block indicated by a dashed line is added. In the following description, except as otherwise explained, a function part having the same reference numeral as in the first embodiment shall have a similar function. Furthermore, FIG. 6 is a view for describing an operation of generating a link in the report generation support apparatus according to this embodiment.

The operator selects an arrow as the type of an annotation before executing first drag-and-drop (a dashed-line arrow 608). Next, the operator selects a string 611 in a comment field 610. Then, the operator designates a drag origin position by placing a pointer on a point 602 on a medical image 601 indicated by the content of the string 611. Then, the operator drags the pointer along the dashed-line arrow 608, and drops the pointer on the string 611. Furthermore, the operator selects an arrow as the type of an annotation before executing second drag-and-drop (a dashed-line arrow 609). Next, the operator selects a string 612 in the comment field 610. Then, the operator designates a drag origin position by placing the pointer on a point 603 on the medical image 601 indicated by the content of the string 612. Then, the operator drags the pointer along the dashed-line arrow 608, and drops the pointer on the string 612. Although the operator executes the drag and drop operation two times as indicated by the dashed-line arrows 608 and 609 in this embodiment as described above, the first drag-and-drop operation and the second drag-and-drop operation are merely different in sign that represents a correspondence relation. Therefore, the configuration and operation will be described below with reference to the first drag-and-drop (dashed-line arrow 608).

The display controller 001 receives designation of the first drag origin position by the operator, and outputs the coordinates of the drag origin point 602 and the coordinates of the position of the medical image 601 to the position specifying part 002. Furthermore, the display controller 001 outputs identification information of the medical image 601 displayed in the drag origin to the annotation generator 003 and a sign attaching part 009. Furthermore, the display controller 001 receives the first drop by the operator, and outputs identification information of the drop destination string 611 to the sign attaching part 009.

The position specifying part 002 obtains the position of the point 602 on the medical image 601, based on the inputted coordinates of the point 602 and the inputted coordinates of the position of the medical image 601. The position specifying part 002 outputs the obtained position of the point 602 on the medical image 601 to the annotation generator 003 and the sign attaching part 009.

The annotation generator 003, based on the inputted type of an annotation, identification information of the medical image 601, and position of the point 602 on the medical image 601, attaches an annotation 605 represented by an arrow to the medical image 601, and stores into the data storage 004.

The sign attaching part 009 previously stores a position from a drag origin point as a position to attach a sign. In this embodiment, it is stored to attach a sign at a position 1 cm above and 0.5 cm right from the drag origin point. The sign attaching part 009 receives input of the identification information of the medical image 601 from the display controller 001 and input of the position of the point 602 on the medical image 601 from the position specifying part 002. The sign attaching part 009 obtains the coordinates of a point 1 cm above and 0.5 cm right from the coordinates of the point 602, as the position to attach an identification sign. Furthermore, the sign attaching part 009 searches the data storage 004 to acquire the number of an identification sign already attached to the medical image 601. Then, the sign attaching part 009 attaches a number subsequent to the number already attached, as a new identification sign. For example, since a first sign is attached in the first drag-and-drop, a sign 606 having the number 1 is the identification sign. Moreover, since the number 1 has been already attached when the second drag-and-drop is executed, a sign 607 having the subsequent number 2 is the identification sign. Then, the sign attaching part 009 attaches the sign 606 to the medical image 601 based on the sign 606 of the obtained identification sign and the position to attach. To be specific, attaching the sign 606 to the medical image 601 is storing, in association with the identification information of a medical image, the display position of the identification sign when the medical image is displayed, into the database of the data storage 004. Furthermore, the sign attaching part 009 receives identification information of the drop destination string 611 from the display controller 001. Then, the sign attaching part 009 attaches a sign 613, which has the same number as the sign 606 attached to the medical image, to the head of a comment including the string 611 based on the identification information of the string 611. To be specific, attaching the sign 606 to the medical image 601 is storing, in association with the identification information of the string, the display position of the identification sign when the string is displayed, into the database of the data storage 004.

The abovementioned operation is executed when the second drag-and-drop (dashed-line arrow 609) is executed. In the second drag-and-drop, a sign 607 having the number 2 is attached to the medical image 601 and a sign 614 having the number 2 is attached to the comment field 610 as the identification signs.

When the operator refers to the comment field 610 of the medical imaging report and clicks the string 611 or 612 therein, the medical image 601 to which the identification sign corresponding to the string and an annotation are attached is displayed on the image viewer 081.

Therefore, when the comment field 610 is displayed on the report display 082 and the medical image 601 is displayed on the image viewer 081, they are displayed in a state that the sings 606 and 613 having the same numbers are attached to the head of the comment having the string 611 and to the periphery of the drag origin point 602. This enables the operator to grasp at a glance that the content of the selected string 611 describes the position indicated by the annotation 604 on the medical image 601. This is true to the string 612. Besides, for example, in a case that the operator designates a triangle as an annotation, an annotation such as an annotation 614 is displayed on a medical image together with an identification sign.

As described above, the report generation support apparatus according to this embodiment is configured to display identification signs having the same numbers (representing a correspondence relation) on a string having link information and on a point in a medical image indicated by the string. Consequently, even if a plurality of annotations corresponding to strings are attached onto a medical image, the operator can easily grasp a point in a medical image corresponding to a certain string. Therefore, the report generation support apparatus according to this embodiment can contribute to increase of the efficiency in interpretation.

Further, although the drag-and-drop operation is executed two times in this embodiment, the report generation support apparatus according to this embodiment can operate even if the drag-and-drop operation is executed one time or more than two times. In the latter case, identification signs that are different for the respective drag-and-drop operations are attached.

Furthermore, although the identification signs are numbers in this embodiment, they may be any signs that make it possible to grasp the correspondence relation between strings and annotations. For example, the identification signs may be characters or may be displayed in different colors.

Third Embodiment

A report generation support apparatus according a third embodiment of the present invention will be described below. The report generation support apparatus of this embodiment is different from that of the first embodiment in that, when a string provided with a link is selected, a generated annotation corresponding to the string is highlighted. Thus, highlighting of a generated annotation corresponding to a string will be mainly described below. A block diagram showing the function of the report generation support apparatus according to this embodiment is similar to the function block of the first embodiment shown in FIG. 1. Except as otherwise explained below, a function part having the same reference numeral as in the first embodiment shall have the same function.

In the report generation support apparatus according to this embodiment, the operation of attaching an annotation and the operation of generating a link are similar to those in the first embodiment.

It is assumed in the following description that the operator clicks a string having link information in a comment field written in a medical imaging report displayed on the report display 082, and displays a medical image corresponding to the string.

The operator selects a string having link information in a medical imaging report displayed on the report display 082 by executing a predetermined operation such as click.

The display controller 001 receives identification information of the selected string, and searches the data storage 004. Then, the display controller 001 acquires identification information of an annotation corresponding to the selected string. The display controller 001 repeatedly displays and hides the annotation corresponding to the selected string to make the annotation blink.

Although an annotation corresponding to a selected string is highlighted by making it blink in this embodiment, it may be highlighted in any other method. For example, an annotation corresponding to a selected string may be highlighted by changing the color of the annotation.

As described above, the report generation support apparatus according to this embodiment is configured to, when a string in a comment field is selected, highlight an annotation corresponding to the string. This enables the operator to easily grasp a portion of a medical image indicated by the content of the selected string. Therefore, the report generation support apparatus according to this embodiment can contribute to increase of the operation efficiency in interpretation.

Further, although the report generation support apparatus according to this embodiment is configured by adding the function to the report generation support apparatus according to the first embodiment, it is also possible to combine with the function according to the second embodiment.

Fourth Embodiment

A report generation support apparatus according a fourth embodiment of the present invention will be described below. The report generation support apparatus of this embodiment is different from that of the first embodiment in that, in response to designation of a region on a medical image, a sign indicating the region is set as an annotation. Thus, designation of a region and generation of an annotation will be mainly described below. A block diagram showing the function of the report generation support apparatus according to this embodiment is similar to the function block of the first embodiment shown in FIG. 1. Except as otherwise explained below, a function part having the same reference numeral as in the first embodiment shall have the same function.

The operator selects a string to which the operator desires to put a link, from a comment field before generating the link by drag-and-drop. Furthermore, the operator designates a region on a medical image corresponding to the content of the string by using the user interface 008. This designation is conducted by, for example, referring to the medical image displayed on the image viewer 081 and surrounding a region to designate with the trajectory of a pointer by using a mouse of the input part 083.

The display controller 001 receives the designation of the region by the operator, and acquires the coordinates of the circumference of the outer edge of the designated region. Then, the display controller 001 receives designation of a position of a drag origin, and outputs the coordinates of the outer edge of the region and the coordinates of the position of the medical image to the position specifying part 002.

Furthermore, the display controller 001 outputs identification information of the medical image 501 after the drag to the annotation generator 003.

The position specifying part 002 receives the input of the coordinates of the outer edge of the region and the coordinates of the position of the medical image from the display controller 001. Then, the position specifying part 002 obtains the position of the outer edge of the selected region on the medical image 301 displayed on the image viewer 081. Then, the position specifying part 002 outputs the obtained position of the outer edge to the annotation generator 003.

The annotation generator 003 receives the input of the identification information of the displayed medical image from the display controller 001. Furthermore, the annotation generator 003 receives the input of the position of the outer edge of the selected region on the medical image from the position specifying part 002.

The annotation generator 003 attaches points to the position of the outer edge of the selected region on the medical image. A group of these points is an annotation. The annotation generator 003 then stores information of the attached annotation 303 into the data storage 004.

Consequently, the medical image is displayed in a state that the annotation indicating the designated region is attached thereto.

As described above, the report generation support apparatus according to this embodiment is configured to display a sign indicating a region designated by the operator, as an annotation. Consequently, it is possible to automatically generate an annotation indicating a region on a medical image that is the content of a string.

Although a configuration in which a function is added to the report generation support apparatus according to the first embodiment is used in the above description, it is also possible to combine with the function according to the second or third embodiment. Moreover, although a configuration in which an annotation is merely attached to the outer edge of a selected region is used in the above description, it is possible to configure so that the operator selects either attachment of an annotation to a drag origin or attachment of an annotation to the outer edge of a region and attaches an annotation based on the selection.

Furthermore, in the respective embodiments described above, as a method for attaching an annotation to a medical image and linking the annotation to a string, a method by drag-and-drop is employed. However, the linking method may be any method as far as it is possible to designate the correspondence between an attached annotation and a string. For example, it is possible to configure to execute the linking by temporarily displaying an annotation in a desired position on a medical image in response to designation of the position on the medical image by the operator, selecting the annotation being displayed, designating a string to be linked to the annotation, and inputting a command to execute the linking by using a link execution button or the like.

Further, in the case of designating a whole report as a link object, it is possible to link an image to the report by designating a position to attach an annotation on an image, dragging from the position, dropping on a key image storing region previously set on the report, and linking the image to the report. At this moment, the annotation is attached to the drag position in the image. A reference image in which the annotation is attached to the drag position may be stored in the key image storing region.

The designation of a position on a medical image and the designation of a report as a link object (in the above description, e.g., an operation from the designation of a position on a medical image to the designation of a key image storing region by drag-and-drop) are equivalent to the "operation input" of "linking the medical image data of the medical image to the medical imaging report" in the present invention.

Further, it is also possible to configure, by setting an image storing region in a report, to attach reduced image data of an image obtained by reducing a medical image (referred to as an "original medical image" here) having been referred to at the time of generation of the report to the image storing region. In such a configuration that the reduced image data is attached, it is possible to designate the reduced image data as a link object.

A case of designating the reduced image data as a link object will be specifically described. The operator designates a position to attach an annotation of an original medical image, and then drags and drops into the image storing region on the report. At this moment, the linking part 007 generates the reduced image data of an image obtained by reducing the original medical image of a drag origin, and stores the generated reduced image data into the image storing region on the report.

Besides, the linking part 007 links the original medical image to the reduced image data stored in the image storing region on the report.

By thus linking an original medical image to reduced image data, a reduced image is displayed in the image storing region when the operator displays the report, and the linked original medical image is read out from the data storage 004 and displayed on the image viewer 081 when the operator selects the displayed reduced image by clinking.

The designation of a position on a medical image and the designation of a reduced image as a link object (in the above description, e.g., an operation from the designation of a position on a medical image to the designation of an image storing region on a report by drag-and-drop) are equivalent to the "operation input" of "linking the medical image data of the medical image to the medical imaging report" in the present invention.

This configuration saves the operator, when referring to an original medical image of a reduced image put on a medical imaging report, from searching the original report, and enables efficient interpretation.

What is claimed is:

1. A report generation support apparatus, comprising:
    A first display configured to display a medical image based on medical image data;
    a second display configured to display a generation screen for generating a string of a medical imaging report;
    a display controller configured to cause the first display and the second display to display an image;
    an operation part for operating a pointer displayed on the first display and the second display;
    an annotation generator including a position specifying part configured to receive designation of a position on the medical image displayed on the first display by using the pointer and specifying the position of the medical image data of a portion corresponding to the medical image at the position, and attach to the medical data, the annotation data representing a position specifying annotation that makes it possible to view the position on the medical image based on the position of the medical image data of the portion specified by the position specifying part;
    an address information acquiring part configured to acquire address information for reading out the medical image data to which the annotation data is attached;
    a linking part configured to link the address information to a link object such as a string designated by using the pointer on the generation screen displayed on the second display; and a sign attaching part configured to base on the designation of the position on the medical image and a designation of the link object corresponding to the designation of the position attach a unique identification sign indicating a correspondence relation between the generated position specifying annotation and the designated link object to the designated position both on the medical image and to a position of the designated link object; wherein when receiving designation of the corresponding link object after the linking, based on designation of the position on the medical image and designation of the link object corresponding to the designation of the position, the display controller refers to the medical image data to which the annotation data linked to the link object is attached and highlights the position specifying annotation indicating the position on the medical image corresponding to the link object.

2. The report generation support apparatus according to claim 1, wherein:
    a display controller receives attachment of the annotation data to the medical image data by the annotation generator, and displays the position specifying annotation based on the attached annotation data, on the medical image displayed on the first display.

3. The report generation support apparatus according to claim 1, wherein:
    the annotation generator receives designation of a region on the medical image, and sets the annotation indicating the designated region as the position specifying annotation.

4. The report generation support apparatus according to claim 3, wherein:
    the annotation generator receives selection of either attachment of the position specifying annotation to the designated position on the medical image or attachment of the position specifying annotation indicating the region, and attaches the selected position specifying annotation.

5. The report generation support apparatus according to claim 1, wherein:
    the annotation generator causes the first display to display a plurality of types of previously stored annotations and, in response to selection of the type of annotation, attaches data indicating a position on the medical image to the selected type of annotation, thereby setting it as the annotation data.

6. The report generation support apparatus according to claim 1, wherein:
    the annotation generator outputs the annotation data to the display controller; and
    the display controller causes the first display to display the annotation data.

7. A report generation support system, comprising:
    a medical image diagnosis apparatus configured to generate a medical image;
    a medical image referring apparatus configured to display a medical image generated by the medical image diagnosis apparatus;
    a report generating apparatus configured to display a screen for generating a medical imaging report based on the medical image displayed by the medical image referring apparatus; and
    an operation part for operating a pointer displayed on a display of the medical image
    referring apparatus and a display of the report generating apparatus, wherein: the medical image referring apparatus has: a position specifying part configured to receive designation of a position on the medical image by using the pointer, and specify the position of medical image data of a portion corresponding to the medical image in the position; and
    an annotation generator including the specified position configured to attach annotation data for representing a position specifying annotation that makes it possible to view the position on the medical image based on the position of medical image data of the specified portion, to the medical image data; and
    the report generating apparatus includes:
    an address acquiring part configured to acquire a storing destination address of the medical image data to which the annotation data is attached; and a linking part configured to, when a link object such as a string displayed on the generation screen is designated by using the pointer, link the storing destination address to the link object; and a sign attaching part configured to, based on the designation of the position on the medical image and a designation of the link object corresponding to the designation of the position, attach a unique identification sign indicating a correspondence relation between the generated position specifying annotation and the designated link object to the designated position both on the medical image and to a position of the designated link object; wherein when receiving designation of the corresponding link object after the linking, based on designation of the position on the medical image and designation of the link object corresponding to the designation of the position, the display refers to the medical image data to which the annotation data linked to the link object is attached and highlights the position specifying annotation indicating the position on the medical image corresponding to the link object.

8. A medical image referring apparatus, comprising: a display configured to display a medical image; an operation part for operating a pointer displayed on the display a position specifying part configured to receive designation of a position on the medical image by using the pointer, and specify the position of medical image data of a portion corresponding to the medical image in the position;

an annotation generator including a position specifying part configured to attach annotation data for representing a position specifying annotation that makes it possible to view the position on the medical image based on the position of medical image data of the specified portion, to the medical image data, and a sign attaching part configured to, based on the designation of the position on the medical image and a designation of the link object corresponding to the designation of the position, attach a unique identification sign indicating a correspondence relation between the generated position specifying annotation and the designated link object to the designated position both on the medical image and to a position of the designated link object; wherein when receiving designation of the corresponding link object after the linking, based on designation of the position on the medical image and designation of the link object corresponding to the designation of the position, the display refers to the medical image data to which the annotation data linked to the link object is attached and highlights the position specifying annotation indicating the position on the medical image corresponding to the link object.

9. A report generation support apparatus, comprising: a first display configured to display a medical image based on medical image data;

a second display configured to display a generation screen for generating a medical imaging report a display controller configured to cause the first display and the second display to display an image;

an operation part for operating a pointer displayed on the first display and the second display;

an annotation generator including a position specifying part configured to, receive designation of a position on the medical image displayed on the first display and specifying the position of the medical image data and in response to operation input of the pointer for linking the medical image data of the medical image displayed on the first display to the medical imaging report, attach, to the medical image data, annotation data representing a position designated by the operation input on the medical image displayed on the first display and making it possible to view the position on the medical image;

a linking part configured to link the medical imaging report to the medical image data for the operation input: and a sign attaching part configured to, based on the designation of the position on the medical image and a designation of the link object corresponding to the designation of the position, attach a unique identification sign indicating a correspondence relation between the generated position specifying annotation and the designated link object to the designated position both on the medical image and to a position of the designated link object; wherein when receiving designation of the corresponding link object after the linking, based on designation of the position on the medical image and designation of the link object corresponding to the designation of the position, the display controller refers to the medical image data to which the annotation data linked to the link object is attached and highlights the position specifying annotation indicating the position on the medical image corresponding to the link object.

10. The report generation support apparatus according to claim 9, wherein the linking part stores the medical image data for the operation input into an image storing region of the medical imaging report for the operation input.

11. The report generation support apparatus according to claim 9, further comprising an address information acquiring part configured to acquire address information for reading out the medical image data for the operation input, wherein the linking part stores reduced image data of the medical image data for the operation input into an image storing region of the medical imaging report for the operation input, and links the address information to the reduced image data.

12. The report generation support apparatus according to claim 9, further comprising an address information acquiring part configured to acquire address information for reading out the medical image data for the operation input, wherein the linking part links the address information for the operation input to at least part of a string of the medical imaging report for the operation input designated and inputted by the operation part.

13. The report generation support apparatus according to claim 9, wherein in response to the attachment of the annotation data by the annotation generator, the first display displays the annotation data.

* * * * *